United States Patent [19]

Buck

[11] 4,360,513
[45] Nov. 23, 1982

[54] SULFONATED POLY(ARYLENE ETHER SULFONE) POLYMERS AS DENTAL PLAQUE BARRIERS

[75] Inventor: Carl J. Buck, Berkeley Heights, N.J.

[73] Assignee: Johnson & Johnson Products, Inc., New Brunswick, N.J.

[21] Appl. No.: 172,487

[22] Filed: Jul. 25, 1980

[51] Int. Cl.$^3$ .................. A61K 7/16; A61K 7/22; A61K 31/315; A61K 31/185
[52] U.S. Cl. ............................. 424/56; 424/54; 424/78; 424/289; 424/315; 424/316
[58] Field of Search .................. 424/49–52, 424/78, 315; 260/505 R, 512

[56] References Cited

U.S. PATENT DOCUMENTS

| | | | |
|---|---|---|---|
| 3,709,841 | 1/1973 | Quentin | 260/2.2 R |
| 3,855,122 | 12/1974 | Bourganel et al. | 264/49 |
| 3,875,096 | 4/1975 | Graefe et al. | 260/29.2 N |
| 3,919,429 | 11/1975 | Grossmann et al. | 424/78 |
| 3,954,677 | 5/1976 | Law | 260/505 R |

FOREIGN PATENT DOCUMENTS 1960812 12/1969 Fed. Rep. of Germany ...... 260/512
1296952 11/1972 United Kingdom .
1507772 4/1978 United Kingdom .

OTHER PUBLICATIONS

Polymer 18, 354–374 (1977)–Attwood et al.
J. Polymer Sci., Part A-1, 5, 2375–2398 (1967) Johnson et al.
J. Applied Poly. Sci. 20, 1885–1903 (1976)–Noshay et al.
Desalination 18, 137–153, (1976)–Brousse et al.
International Publ. No. WO79/00456–1979–Chang.

Primary Examiner—Douglas W. Robinson

[57] ABSTRACT

Compositions and methods for preventing the attachment of dental plaque to the surfaces of the teeth of mammals comprise certain sulfonated poly(arylene ether sulfone) polymers and the pharmaceutically acceptable salts thereof in a pharmaceutically acceptable vehicle, and the periodic application thereof to teeth.

6 Claims, No Drawings

SULFONATED POLY(ARYLENE ETHER SULFONE) POLYMERS AS DENTAL PLAQUE BARRIERS

TECHNICAL FIELD

This invention relates to oral hygiene compositions and methods using such compositions to prevent attachment of bacteria to teeth. More particularly, it relates to certain sulfonated polymeric materials that have been found useful in inhibiting the agglutination of oral microbes on teeth.

BAACKGROUND ART

The prevention of the deposition of dental plaque on teeth is a highly desired result. Dental plaque results when cariogenic bacteria aggregate in colonies on the surface of teeth and form a tenacious deposit thereon. The presence of plaque on teeth is believed to be a precursor to development of gingivitis, dental caries and periodontal disease.

While many attempts have been made to control the effects of cariogenic bacteria and the dental plaque they produce, for example, fluoride, flossing, brushing, etc., treatments, these are typically directed to either counteracting the secondary effects of plaque on the teeth and gums, or to the removal of plaque that is already formed on and adhering to the teeth and surrounding tissue. Such treatments are not, however, entirely successful, and must be supplemented with periodic treatment by dental professionals. To date, there is no commercially feasible home treatment method for preventing the formation of plaque or its adhesion to teeth.

THE INVENTION

A number of hydrophilic sulfonic acid and sulfonic acid salt derivatives of certain poly (arylene ether sulfone) polymers have been synthesized and found to inhibit the deposition of dental plaque onto human teeth. These hydrophilic polymeric sulfonates have good film forming characteristics and, accordingly, are applied to teeth from various dentifrice formulations, mouth rinses, or other oral hygiene procedures. The sulfonate polymers of this invention are anionic in nature and substantially soluble in water or water/organic solvent vehicles, primarily because of the relatively high degree of sulfonation achieved during preparation of these derivatives. While the mechanism of action of the hydrophilic polymeric films in retarding plaque deposition is not known with absolute certainty, it is presumed that the films of anionically-charged polymers deposited on teeth effect a mutual repulsion between the negatively charged polymer film and the negatively charged microorganisms in oral fluids responsible for plaque generation. For example, when powdered human dental enamel is dispersed in the aqueous media containing salts of the polymeric sulfonates, a substantially negative surface charge is imparted to the enamel particles, as determined by zeta potential measurements. The sulfonated poly (arylene ether sulfone) polymers of this invention are especially effective as components of dentifrices and other oral hygiene preparations in reducing dental plaque deposition on teeth.

Hydrophilic, polymeric, anionic sulfonates useful for dental plaque control in accordance with the present invention are prepared by aromatic sulfonation of poly (arylene ether sulfone) polymers, followed by conversion of the polymeric sulfonic acid derivatives to metal salts of certain of the Group IA alkali metals, Group IIA, IIB, and IIIA multi-valent metals, and ammonium or amine-salts. The repeating units of the sulfonated poly(arylene ether sulfone) polymers of this invention are selected from the group consisting of structure (A),

   (A)

and structure (B),

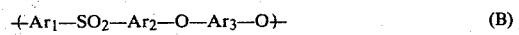   (B)

wherein $Ar_1$ and $Ar_2$ are each selected from

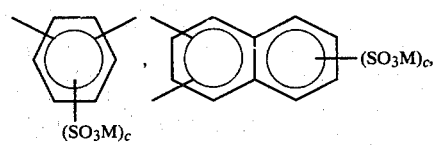

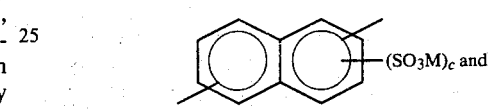

provided further that $Ar_2$ also can comprise one or more spacing units selected from —$Ar_4$—$SO_2$—$Ar_4$— and —$Ar_4$—$SO_2$—$Ar_4$—$SO_2$—$Ar_4$—, each $Ar_4$ in said spacing units being separately selected from

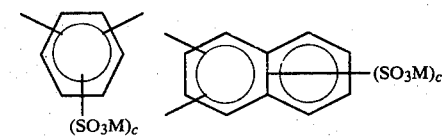

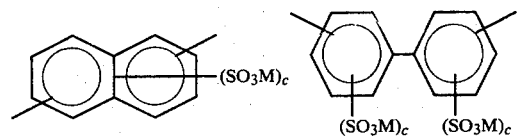

$Ar_3$ is selected from $Ar_4$ and

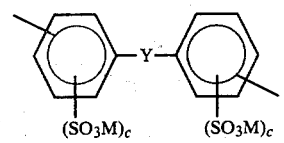

where Y is selected from lower alkylene having 1–5 carbon atoms, lower alkylidine having 2–5 carbon atoms,

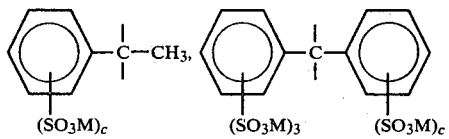

O, S, and SO₂; subscript c being an integer selected from 0, 1, and 2, the quotient, obtained by dividing the total number of sulfonate groups (i.e. the sum of the c's within each of repeating units (A) and (B) by the number of aromatic groups in said repeating unit, being (on the average) at least about 0.2; and M is selected from the group consisting of lithium, sodium, potassium, calcium, magnesium, zinc, aluminum, hydrogen, ammonium, and substituted ammonium ions derived from pharmaceutically acceptable organic amines.

In general, the metal and ammonium salts are preferred over the free sulfonic acid forms of the polymers because of their higher water solubility and lower degree of acidity, thereby favoring their use in oral hygiene formulations as dental plaque control barriers. The zinc salts are particularly preferred.

The polymers utilized for conversion to sulfonate derivatives are available either commercially or synthesized by known procedures found in the literature. Representative examples of commercial poly (arylene ether sulfone) polymers wich can be sulfonated to the hydrophilic, anionic sulfonates of this invention are the following:

(a) Udel ® Polysulfone, type P1700 or medical grade MG11, available from Union Carbide Corp. in a molecular weight of about 35,000, and having the following repeating unit structure:

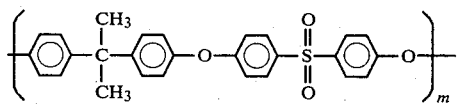

(b) Victrex ™ Polyethersulfone, grades 100P, 200P, 300P, from ICI America, Inc.:

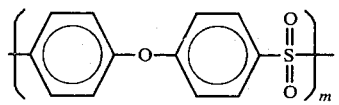

(c) Radel ® Polysulfone from Union Carbide Corp., and thought to have the following repeating unit structure:

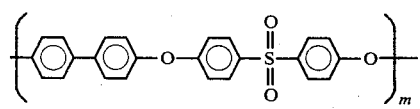

The generalized structures for other poly (arylene ether sulfone) polymers that can be sulfonated to form the sulfonated polymers of this invention are represented as formulas (I) and (II), and their method of synthesis is indicated in equations (1) and (2) below:

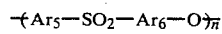      (I)

      (II)

      (1)

      (2)

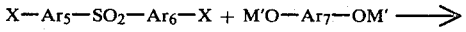

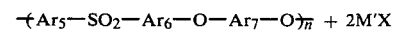

wherein

X is a halogen; M' is a univalent metal such as sodium or potassium;

Ar₅ and Ar₆ are each selected from

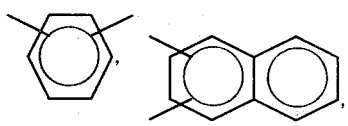

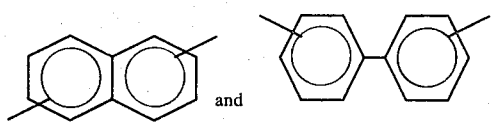

provided further that Ar₆ also can comprise one or more spacing units selected from —Ar₈—SO₂—Ar₈— and —Ar₈—SO₂—Ar₈—SO₂—Ar₈—, each Ar₈ in said spacing units being separately selected from

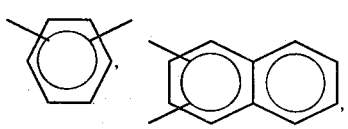

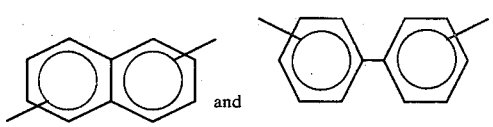

Ar₇ is selected from Ar₈ and

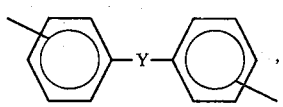

where Y is selected from lower alkylene having 1-5 carbon atoms, lower alkylidine having 2-5 carbon atoms,

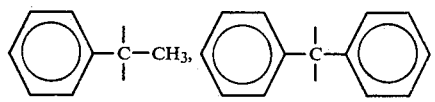

O, S, and SO₂.

Polymers of structure (I) can be synthesized by the general procedure (summarized in equation (1) above) described by T. E. Attwood, et al., in Polymer, Volume 18, pages 354–374 (1977). Polymers of structure (II) are prepared by reaction of bis(haloaryl) sulfones with univalent metal salts of aromatic diols, such as the reaction taught by R. N. Johnson, et al., J. Polymer Science, Part A-1, Volume 5, pp. 2375-2398 (1967). Poly (arylene ether sulfone) polymers suitable for conversion to sulfonated derivatives for use in the compositions and method of the present invention can be synthesized by varying the nature of the aromatic group, orientation of the linkages of the aromatic ring, and spacing of the sulfone ($SO_2$), ether (O) and other connecting groups in accordance with the foregoing definitions of the aromatic polymeric structures (I) and (II).

The sulfonation of poly (arylene ether sulfone) polymers, such as Udel ® Polysulfone, to water insoluble sulfonated polymers with low degrees of sulfonation, and suitable as membranes for water desalination, have been described in the literature and patent publications such as A. Noshay and L. M. Robeson, J. Applied Polymer Science, 20, 1885-1903 (1976); C. L. Brousse, et al., Desalination, 18, 137-153 (1976); and U.S. Pat. Nos. 3,709,841 (issued Jan. 9, 1973), 3,855,122 (issued Dec. 17, 1974), and 3,875,096 (issued Apr. 1, 1975). These sulfonates polysulfones differ from the derivatives of the present invention in that they are substantially water insoluble, due to the relatively low degree of sulfonation, and therefore cannot be utilized in the aqueous media required for oral hygiene applications. As will be described hereinafter, the poly(arylene ether sulfone) sulfonates of the present invention are substantially soluble in water or mixed solvents comprising water and an organic solvent miscible therewith (generally at least 1% w/w) and hydrophilic as a consequence of their higher degree of sulfonation. As discussed in greater detail hereinafter the degree of sulfonation (D.S.) also has a significant effect on the extent of dental plaque deposition. D.S. as used herein is the average number of sulfonate or sulfonic acid groups per repeating unit of the polymeric structure.

Preferred sulfonation agents for preparing the sulfonated polymeric barriers of this invention are anhydrous sulfur trioxide, triethyl phosphate (TEP) complexes of sulfur trioxide, and chlorosulfonic acid. due to the high reactivity of sulfur trioxide and its potent dehydration properties, sulfonation reactions with sulfur trioxide sometimes result in formation of highly insoluble polymer dispersions due to crosslinking caused by inter-polymer chain sulfone formation. In these situations, it is preferable to moderate the sulfonation reactivity by utilization of the sulfur trioxide complexes with triethyl phosphate (TEP), which minimize or essentially eliminate formation of crosslinked by-products [cf. A. F. Turbak, Ind. Eng. Chem., Prod. R & D, 1, 275(1962); U.S. Pat. No. 3,072,619 (Jan. 8, 1963); A. F. Turbak and A. Noshay, U.S. Pat. No. 3,206,492 (Sept. 14, 1965); N. H. Canter, U.S. Pat. No. 3,642,728 (Feb. 15, 1972); A. Noshay and L. M. Robeson, J. Applied Polymer Science, 20, 1885-1903 (1976)]. While the sulfonation activity increases with the molar proportion of sulfur trioxide in the complex with TEP, mole ratios of 2:1, 3:1, and 4:1 are preferred for the synthesis of the poly (arylene ether sulfone) sulfonates of the present invention. In some instances where it is difficult to effect sulfonation under milder conditions with the complexes, sulfonation with sulfur trioxide (alone) or chlorosulfonic acid is more effective.

Sulfonations can be effected in solvents such as methylene chloride, 1,2-dichloroethane, and chloroform, since these are generally good solvents for the starting aromatic polymer and poor solvents for the sulfonated polymer, which precipitates directly from the reaction medium and is filtered. In those instances where the product is soluble in the reaction medium and did not precipitate, the sulfonated polymer is isolated by removing the solvent and converted to well-defined solids by either trituration or slurrying with an appropriate non-solvent.

Three modes of reacting the sulfonation agent and polymer were examined: (1) addition of sulfonation agent to polymer, (2) addition of polymer to the sulfonation agent, and (3) simultaneous addition of the sulfonation agent and polymer to the reaction medium. Methods (1) and (3) are preferred, since addition of the polymer to the sulfonation agent (method 2) sometimes gives rise to non-uniform products, probably because of the large excess of sulfonation agent present during the early stages of the reaction. The most preferred sulfonation process is that of method (3), involving simultaneous additions of the reactants. These conditions afford sulfonated products of greater uniformity and which often precipitate directly from the reaction as finely divided solids, thereby minimizing occlusion of solvent, residual acids, complexing agents (e.g., triethyl phosphate), and unreacted polymer by the sulfonated polymer.

Temperature control of the sulfonation reaction with sulfur trioxide and its complexes with TEP is not very critical. Acceptable results are obtained over a $-20°$ C. to $+40°$ C. range. Sulfonations are generally effected at ambient room temperatures, since the sulfonation exotherm is very mild and rarely results in temperature increases beyond 35° C.

Typical impurities in the sulfonated polymer are small amounts of unreacted polymer, excess sulfonation agent (as sulfuric acid), and residual triethyl phosphate which are occluded in the solid polymer. Substantial purification is effected by slurrying the polymeric sulfonic acid derivatives in non-solvents therefor, such as the halocarbons.

Removal of the free sulfuric acid is difficult, since it complexes strongly with the polymeric product. It has been found that diethyl ether is an exceptionally good complexing agent for sulfuric acid and effectively removes this contaminant when freshly isolated polymeric solids are slurried in the ether and filtered. Other effective additives for sulfuric acid removal are halocarbon solvent blends with diethyl ether and other oxygenated solvents, such as ethyl acetate and acetone. The sulfuric acid, if not removed, results in contamination of the metal salts prepared by neutralization or ion-exchange reactions on the polymeric sulfonic acid intermediates, with considerable inorganic sulfate, such as sodium sulfate, in the case where the sodium sulfonate polymer is produced.

Efficient purification of the sulfonic acid derivatives of the polymers is not always possible, but it has been found that additional purification results in conversion of the sulfonic acid groups to their various salts of monovalent and divalent metal atoms. For example, neutralization of an ethanol solution of Udel ® polysulfone sulfonic acid of D.S. 1.8 with alcoholic sodium hydroxide results in precipitation of the sodium sulfonate salt in a higher state of purity. Much of the occluded triethyl phosphate and any processing solvents are freed to the filtrate during precipitation of the product.

The preferred process for purification of the sulfonated polymers (both free acids and salts), particularly highly water soluble types, is by dialysis of their aqueous solutions in membrane tubes or hollow fiber dialyzing units having a molecular weight cut-off well below the molecular weight of the polymer. Dialysis removes all of the low molecular weight impurities, triethyl phosphate, and inorganic salts. High purity polymers are isolated as solids by freeze-drying or spray drying the dialyzed polymer solution.

Examples of acceptable metal salts of the polymeric sulfonic acid derivatives of poly (arylene ether sulfone) polymers in accordance with this invention are the potassium, lithium, sodium, calcium, magnesium, zinc, and aluminum salts. The zinc salts are particularly preferred, since they exhibit higher substantivity to human dental enamel (after repeated washings with water) than the alkali metal salts. Other acceptable salt forms of the polymers are the ammonium salts prepared from ammonia or pharmaceutically-acceptable organic amines.

The alkali metal salts of the sulfonated polymers are conveniently prepared by neutralization of a water or alcohol solution of the polymeric sulfonic acid derivative with alkali metal hydroxide solutions to the potentiometric endpoint. The salts are recovered by filtration, solvent stripping, or freeze drying, depending on the type of solvent used and whether the salt precipitates directly from the solvent medium. Alternatively, sulfonate salts can be prepared by addition of at least stoichiometric quantities of an alkali metal oxide, carbonate, acetate, chloride, nitrate, or sulfate to the sulfonic acid derivative. The salts either precipitate directly, or are isolated by solvent stripping. Purification of the sulfonate salt by dialysis is the preferred procedure for the more highly water soluble salts.

Multivalent metal salts, such as the calcium, magnesium, zinc, and aluminum salts, of the sulfonated polymers can be prepared by methods similar to those described above. In an alternate procedure, multivalent metal salts can be prepared by an ion-exchange reaction between the multivalent ion and either the free sulfonic acid or an alkali metal sulfonate derivative of the polymer. The neutralization and other salt forming reactions described above are essentially ion-exchange reactions, as typified by the following equations, where P represents the polymer chain:

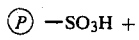 —SO$_3$H +

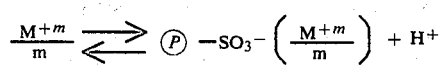

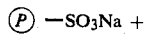 —SO$_3$Na +

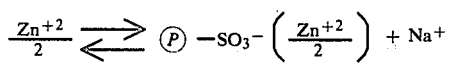

Ammonium salts of the sulfonic acid polymer can be prepared by direct addition of ammonia or a primary, secondary, or tertiary organic amine.

The polymeric sulfonic acids of the present invention are highly effective in reducing the deposition of plaque during in vitro testing, but these sulfonic acid polymers are too highly acidic to permit use in the oral environment unless suitably buffered. Various salts of the polymeric sulfonic acids are preferred because of their increased solubility in aqueous media and lower degree of acidity. These salts exhibit approximately equivalent reduction of plaque deposition to that exhibited by the corresponding free acids when tested in vitro.

The in vitro test procedure we have employed begins with growth of plaque in small jars containing sterilized trypticase media that has been supplemented with sucrose. Typically, ten jars are individually inoculated with 0.5 ml of unpooled freshly collected human plaque from 10 subjects. In a control series, a presterilized glass slide or an extracted human tooth is inserted into each jar. In the test series, the tooth or glass slide is pretreated with a 1% solution of the test compound (dissolved in water or other vehicle), allowed to dry in order to deposit a thin film or the compound on the surface, and the glass slide or tooth placed in the growth media. The jars are incubated under anaerobic conditions for two days at 37° C. The tooth or glass slide is removed, air dried, and stained with 0.15% FD&C #3 red dye solution to reveal the accumulated plaque deposits. The tooth or glass slide is scored for plaque density on a 0 to 5 scale against the control. Plaque barrier activity is reported as the % of average plaque reduction, as compared to appropriate controls for ten subjects.

The degree of sulfonation of the poly (arylene ether sulfone) polymer has a significant effect on the reduction of plaque deposition, and it is found that a certain minimal D.S. is required for development of adequate plaque barrier activity. The D.S. can be varied at will by adjusting the conditions of the sulfonation reaction, such as the molar ratio of sulfonating agent to polymer. The nature of the aromatic polymer repeating unit governs the maximum D.S. which can be achieved. Linking groups, such as ether, sulfone, and various organic radicals (see e.g. the definition of Y set forth above) attached to the aromatic rings in the polymer chain structure can have either a deactivating or activating effect on aromatic sulfonation. Electronic and steric effects determine the position of sulfonation as well as ease of sulfonation. These mechanistic considerations have been reviewed in general organics texts, such as that by R. T. Morrison and R. N. Boyd, "Organic Chemistry," Third Edition, Allyn and Bacon, Inc., Boston, 1973. In the poly (arylene ether sulfone) polymers, the ether linkages activate sulfonation in the available ortho-positions of the adjoining aromatic rings; in contrast, the sulfone group will deactivate the aromatic rings to which it is bonded with respect to aromatic sulfonation. A. Noshay and L. M. Robeson (supra) have established, for example, that sulfonation of Udel ® Polysulfone indeed takes place only in the ortho-positions of the Bisphenol A moiety relative to the ether oxygen atoms, e.g.,

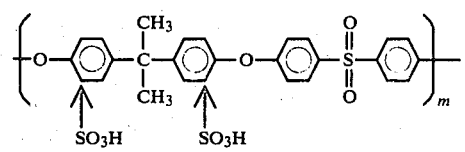

The degree of sulfonation (D.S.) of the poly(arylene ether sulfone) derivative can be determined by any of several methods: (a) NMR analysis, (b) elemental analysis for sulfur to carbon ratio, or (c) direct titration of the sulfonic acid with standard sodium hydroxide. The NMR method is perhaps the more exact procedure, since it is not prone to interference by other impurities, such as with the acidimetric or elemental analyses. Acidimetric assays for D.S. agreed well with those determined via NMR when the sulfonic acid polymer is carefully washed free of entrapped sulfuric acid and thoroughly dried and, in this regard, is often the most convenient assay method for monitoring the progress of the sulfonation reaction. Good correlation between calculated and theoretical values for the metal salt content, determined by atomic absorption, is obtained on polymers carefully purified by dialysis.

The acidimetric procedure for D.S. determination involves titration of an accurately weighed two gram sample (±0.1 mg) of the sulfonic acid polymer, dissolved in about ten volumes of water, alcohol, or other solvents, with standardized sodium hydroxide to the potentiometric endpoint. The acidity, A, of the samples is expressed in milliequivalents/gram (meq/g). Using the acidity value, A., and the formula weight, R, of the unsulfonated repeat unit in the polymer, the D.S. is calculated from the following equations:

$$A = \frac{(ml.\ of\ titrant)\ (Normality)}{sample\ weight,\ in\ grams}$$

$$D.S. = \frac{(R)\ (A)}{1000 - 80A}$$

A related concept to D.S. which is sometimes more useful in correlating polymer structure with plaque barrier activity is the average number of sulfonate or sulfonic acid groups per aromatic group in the repeating unit. This is simply the D.S. (as determined by the aforementioned procedures) divided by the number of aromatic groups in the repeating unit, i.e., D.S./Ar. For example, Udel ® Polysulfone sodium sulfonate of D.S. 2.0 can be expressed as exhibiting a D.S./Ar of 0.5, since there are four aromatic groups within each repeating unit.

The plaque barrier activity of the sulfonated salts of the poly (arylene ether sulfone) polymers, such as those of Udel ® Polysulfone, Vitrex ™ Polyethersulfone, and Radel ® Polysulfone are shown in Table 1 and demonstrate the necessity of achieving a certain minimum extent of sulfonation in order to obtain satisfactory plaque barrier activity. Generally, sulfonated poly (arylene ether sulfone) polymers of high plaque barrier activity are obtained only when the average number of sulfonate groups per aromatic group (D.S./AR) within the polymer is at least about 0.2. Aside from being insoluble in water, the non-sulfonated polymeric intermediates exhibit no plaque barrier properties whatsoever. Effective plaque barrier activity (plaque reduction of at least above 40%) is seen only when the hydrophilic properties of the polymer are increased by introduction of either sulfonic acid or sulfonate salt functional groups.

While the molecular weight of the polymers used in the compositions of the present invention is not considered to be a critical factor, they generally have a weight average molecular weight within the broad range of from about 5,000 to about 200,000. A preferred molecular weight range is from about 20,000 to about 50,000.

TABLE 1

Effect of Degree of Sulfonation (D.S.) on Plaque Barrier Activity of Typical Poly (Arylene Ether Sulfone) Sulfonates

| General Structure | M | D.S. | D.S/AR | % Plaque Reduction |
|---|---|---|---|---|
| (structure with CH₃—C—CH₃, O, S(=O)₂) | (Control) | 0 | 0 | 0 |
| (structure with SO₃M CH₃ SO₃M, O, S(=O)₂) | H | 0.8 | 0.2 | 78 |
|  | H | 1.6 | 0.4 | 50–69 |
|  | H | 2.0 | 0.5 | 70–76 |
|  | Na | 0.4 | 0.1 | 0 |
|  | Na | 0.6 | 0.15 | 74 |
|  | Na | 1.0 | 0.25 | 64–70 |
|  | Na | 1.5 | 0.4 | 78–82 |
|  | Na | 2.0 | 0.5 | 89 |
|  | K | 1.8 | 0.45 | 87 |
|  | Li | 1.8 | 0.45 | 87 |
|  | Ca | 1.8 | 0.45 | 52 |
|  | Zn | 1.8 | 0.45 | 85 |
|  | Al | 2.0 | 0.5 | 66 |
| (structure with SO₃M, O, S(=O)₂) | Na | 0.2 | 0.1 | 0–4 |
|  | Na | 0.4 | 0.2 | 62–69 |
|  | Na | 0.5 | 0.25 | 76 |
|  | Na | 0.6 | 0.3 | 78 |
|  | Na | 0.8 | 0.4 | 72–84 |
|  | Na | 1.0 | 0.5 | 66 |
|  | H | 0.6 | 0.3 | 86 |
|  | Na | 0.6 | 0.3 | 75–86 |

TABLE 1-continued

Effect of Degree of Sulfonation (D.S.) on Plaque Barrier Activity of Typical Poly (Arylene Ether Sulfone) Sulfonates

| General Structure | M | D.S. | D.S/AR | % Plaque Reduction |
|---|---|---|---|---|
| (structure with SO₃M SO₃M groups) | Na | 1.6 | 0.4 | 89 |

EXAMPLE 1

Udel ® Polysulfone Sulfonic Acid, D.S. 1.8

A 12 liter resin flask was fitted with a mechanical stirrer, thermometer, two addition funnels, and a nitrogen inlet adapter. The flask was charged with 3000 ml. methylene chloride which was dried over molecular sieves. Into one of the addition funnels was charged a solution of 664 g (1.50 moles) Udel ® Polysulfone (type P1700, medical grade, MG 11; Union Carbide) in 3000 ml. dry methylene chloride. Into the other addition funnel was charged the sulfonation agent, prepared by controlled addition of 360 g (4.50 moles) anhydrous liquid sulfur trioxide to a cooled solution of 205 g (1.125 moles) triethyl phosphate dissolved in 3000 ml. dry methylene chloride.

While stirring the methylene chloride solvent in the resin flask, the solutions of the polymer and sulfonation agent were added simultaneously over one to two hours at the ambient temperature, varying from 23° to 32° C. After the additions were completed, the resultant suspension of white solids was stirred another one to two hours at the ambient temperature. The product was vacuum-filtered on a glass-fritted funnel, washed three times with 4 liters of methylene chloride by mechanical slurry and filtered each time. A final slurry wash in anhydrous diethyl ether whitened the product. After air drying at room temperature the yield of the sulfonic acid derivative of Udel ® Polysulfone was 1043 grams. The degree of sulfonation (D.S.), determined by acidimetric titration or NMR analysis, was 1.8.

EXAMPLE 2

Udel ® Polysulfone Sodium Sulfonate, D.S. 1.8

A stirred solution of 1030 grams of the sulfonic acid derivative, prepared according to Example 1, in 5150 ml. 95% ethanol, was stirred vigorously during slow addition of 2 N sodium hydroxide (in ethanol) to the neutralization endpoint (pH 8-9). The suspension of the sodium sulfonate derivative was stirred another hour, suction filtered, washed with 95% ethanol on the funnel and subsequently by mechanical slurry in 2000 ml. 95% ethanol. The solids were air dried at room temperature to remove most of the solvent before final drying in a forced air oven at 60° C. to near constant weight. The yield of the sodium sulfonate derivative, D.S. 1.8, of Udel ® Polysulfone was 1041 grams.

EXAMPLE 3

Udel ® Polysulfone Zinc Sulfonate, D.S. 1.8

A stirred suspension of 133.0 g Udel ® Polysulfone sodium sulfonate derivative, D.S. 1.8, prepared as in Example 2, in 1200 ml. water was heated to dissolve the polymer, cooled to room temperature, and the solution centrifuged to remove about 4% of highly insoluble solids. An aliquot of the total centrifugate containing about 26.3 g sodium sulfonate solids was diluted to about 500 ml. with water. A solution of 10.5 g zinc chloride in 20 ml. water was added and the resultant hazy solution, pH 6.2, dialyzed in a membrane tube (6000-8000 molecular weight cut-off) surrounded with distilled water for two days. Removal of the water from the dialyzed polymer solution, pH 6.5, by freeze drying gave 25.4 g of purified Udel ® Polysulfone zinc sulfonate, D.S. 1.8, as fluffy white solids.

In an alternate procedure, the solution of the sodium sulfonate derivative in water is prepared and centrifuged after addition of the zinc chloride to give a clarified solution of the zinc sulfonate derivative. Further purification is effected, particularly on a larger scale, by continuous dialysis through a Tri-Ex-1 Hollow Fiber Dialyzer (Extracorporeal Medical Specialties, Inc.) using two passes through the dialyzer at a polymer solution flow rate of 100-200 ml/minute and countercurrent distilled water flow rate of about 500-600 ml/minute. The dialyzed polymer solution is freeze dried to afford the purified polymeric zinc salt.

The polymeric zinc salt was quite hygroscopic and absorbed considerable water (35-40% weight gain) when exposed to relative humidities of both 42 and 75% for about 24 hours. To stabilize the water content of a bulk supply of polymer for clinical studies, the zinc sulfonate obtained via freeze drying was deliberately exposed to laboratory ambient conditions (at a temperature in the range of about 20°-25° C. and relative humidities that ranged between about 40 and 70%) to allow for maximum moisture uptake for several days to substantially constant weight. Using this procedure, an 8 kg. lot of zinc salt was equilibrated to a water content of 21.5% by weight, as determined by thermogravimetric analysis.

The assay values for this lot of polymeric zinc salt are shown in Table 2 and, when corrected for the water content, agreed very well with the theoretical values for the anhydrous zinc salt having a D.S. of 1.8.

TABLE 2

Analytical Data on Udel ® Polysulfone Zinc Sulfonate, D.S. 1.8

| Assay | Found "As Is" | Found "Anhydrous Basis" | Theory For D.S. 1.8 |
|---|---|---|---|
| Carbon, % | 39.83 | 50.73 | 50.38 |
| Hydrogen, % | 3.71 | 3.19 | 3.16 |
| Sulfur, % | 11.0 | 14.1 | 13.95 |
| Zinc, % | 7.0 | 8.9 | 9.14 |
| Water, % | 21.5 | 0 | 0 |
| Chloride, % | 0.094 | 0.12 | 0 |
| Sodium, % | 0.36 | 0.46 | 0 |
| Phosphate (as Triethyl Phosphate) | 0.27 | 0.34 | 0 |
| Sulfate, %, | Not | — | 0 |

TABLE 2-continued

Analytical Data on Udel ® Polysulfone Zinc Sulfonate, D.S. 1.8

| Assay | Found "As Is" | Found "Anhydrous Basis" | Theory For D.S. 1.8 |
|---|---|---|---|
| as $Na_2SO_4$ | found | | |
| Absorptivity at 272 nm | 26.78 | 34.11 | — |
| D.S. via NMR | 1.8 | 1.8 | 1.8 |
| pH, 1% in water | 6.9 | — | — |

EXAMPLE 4

Udel ® Polysulfone Zinc Sulfonate, D.S. 1.8, Via Ion-Exchange of The Sulfonic Acid Derivative A solution of 5.0 g of the Udel ® Polysulfone sulfonic acid derivative (16.6 milliequivalents of acidity) in 100 ml. water was prepared and, after addition of 2.25 g (33.0 meq.) zinc chloride, was allowed to stand at room temperature overnight to allow ion-exchange to proceed. The solution was clarified by filtration on an 0.8 micron membrane filter and the filtrate dialyzed in a dialysis membrane tube (M.W. 12,000 cutoff) in water. The hydrochloric acid by-product formed in the ion-exchange reaction was removed to the extent of 94% within one hour of dialysis, as determined by titration of the surrounding water (pH2.7) with sodium hydroxide. The dialysis was allowed to proceed several days, and the purified polymer solution stripped free of water under reduced pressure to give 3.7 g of the hygroscopic zinc sulfonate derivative of Udel ® Polysulfone. Analysis: Zinc, 7.08%; Sodium, 0.026%; Absorptivity at 274 nm, 31.9; sulfate and triethyl phosphate were not detectable.

EXAMPLE 5

Udel ® Polysulfone Sodium Sulfonate, D.S. 0.7

Solutions of 2.2 g (5.0 m moles) polysulfone in 20 ml. dry methylene chloride and 0.33 ml (0.58 g, 4.98 m moles) chlorosulfonic acid in 20 ml. methylene chloride were added simultaneously, with stirring, to 40 ml. methylene chloride in the reaction flask. The addition time was 21 minutes and the temperature remained constant at 24° C. The pink solution, containing some gummy deposits, was stirred another hour and was diluted with 100 ml. diethyl ether. The clear solution phase was decanted from the gum. On trituration with additional ether, the gum converted to white solids which were collected, washed with ether, and dried to afford 2.5 g of polysulfone sulfonic acid. The D.S., determined by titration of a 2.4925 g sample of the sulfonic acid in 1:1 tetrahydrofuran-water to the neutralization endpoint with 6.9 ml. 0.495 N sodium hydroxide solution, was 0.7. Solvent stripping of the neutralized solution gave 2.3 g of the sodium sulfonate derivative of the polysulfone.

EXAMPLE 6

Poly (phenylene ether sulfone) Sodium Sulfonate, D.S. 0.6

A solution of 2.32 g (10.0 m moles) poly (p-phenylene ether sulfone), type 100 P (ICI), in 40 ml. dry methylene chloride was added over 21 minutes, at 24°–25° C., to a stirred solution of 1.6 g (20.0 m moles) liquid sulfur trioxide in 80 ml. methylene chloride. After an additional reaction period of 20 minutes, the reaction mixture was diluted with 20 ml. diethyl ether and the white solids collected. The solids were washed by slurrying in 150 ml. methylene chloride, filtered, and washed with methylene chloride and ether. The yield of the sulfonic acid derivative was 2.8 g.

Neutralization of a 2.511 g sample of the sulfonic acid derivative in methanol-water with 8.0 ml. 0.641 N sodium hydroxide solution established that the degree of sulfonation (D.S.) was 0.6. Removal of the solvents from the neutralized solution gave 2.5 g of the sodium sulfonate derivative of the polymer.

EXAMPLE 7

Radel ® Polysulfone Sodium Sulfonate, D.S. 1.3

To a stirred suspension of 4.0 g (0.01 mole) powdered Radel ® Polysulfone in 40 ml. dry methylene chloride was added, over 12 minutes at 24°–26° C., a solution of 2.4 g (0.03 mole) liquid sulfur trioxide dissolved in 20 ml. methylene chloride containing 1.37 g (7.5 m mole) triethyl phospate. The suspension was stirred another 70 minutes at 24°–26° C. and allowed to stand at room temperature for three days. The solids were filtered, washed with methylene chloride and diethyl ether, and dried to give 3.6 g of the sulfonic acid derivative of the polymer.

The sodium salt was prepared by neutralization of a stirred suspension of 3.5507 g of the sulfonic acid derivative in 10 ml. methanol with standardized sodium hydroxide solution. The solids suspension of the sodium salt was recovered by solvent stripping, dissolution of the residue in 1:1 tetrahydrofuran-water, filtration from some solids (0.5 g) believed to be sodium sulfate, and solvent stripping of the resultant filtrate to fine, tan colored solids weighing 2.3 g. The D.S., corrected for the amount of free sulfuric acid in the sulfonic acid polymer which was recovered as sodium sulfate, was 1.3. The D.S. determined by NMR analysis was 1.6.

The plaque barrier oral compositions of this invention may comprise any conventional pharmaceutically acceptable oral hygiene formulation that contains (and is compatible with) an effective amount of a plaque barrier agent as defined herein. Such formulations include, for example, mouthwashes, rinses, irrigating solutions, abrasive and nonabrasive gel dentifrices, denture cleansers, coated dental floss and interdental stimulator coatings, chewing gums, lozenges, breath fresheners, foams and sprays.

The plaque barrier agents may be present in these formulations in effective concentrations generally in the range of from about 0.05 weight percent to as much as 30 weight percent or the limit of compatibility with the vehicle. However, no advantage will be derived from concentrations in excess of about 20 weight percent. A preferred concentration range for the plaque barrier agents in the formulations of the invention is from about 0.5 to about 10 weight percent. A more preferred range is from about 2 to about 8 percent by weight, about 5% being the presently most preferred concentration in a nonabrasive gel vehicle.

The pH of these plaque barrier preparations should be between pH 5.0 and 10.0, preferably between pH 5.0 and 8.0, more preferably between about pH 6.0 and 7.5. Lower pH than 5.0 is undesirable because of the possible enhancement of enamel demineralization.

Suitable conventional pharmaceutically acceptable vehicles that can be employed with the plaque barrier agents to prepare the barrier compositions of this invention may comprise water, ethanol; such humectants as polypropylene glycol, glycerol and sorbitol; such gelling agents as cellulose derivatives, for example, Methocel, carboxymethylcellulose (CMC 7MF) and Klucel HF, polyoxypropylene/polyoxyethylene block copolymers, for example, Pluronic F-127, Pluronic F-108, Pluronic P-103, Pluronic P-104, Pluronic P-105, and Pluronic P-123, colloidial magnesium aluminosilicate complexes such as Veegum, and mucoprotein thickening agents such as Carbopol 934; gel stabilizers such as the silicon dioxides, for example, Cab-O-Sil M5, and polyvinylpyrrolidone; sweeteners such as sodium saccharin; preservatives such as citric acid, sodium benzoate, cetylpyridinium chloride, potassium sorbate, methyl and ethyl parabens; detergents such as sodium lauryl sulfate, sodium cocomonoglyceride sulfonate, sodium lauryl sarcosinate and polyoxyethylene isohexadecyl ether (Arlasolve 200) and approved colors and flavors.

The following specific examples will serve further to illustrate the plaque barrier compositions of this invention.

EXAMPLE A - Mouthwash Solution

| | |
|---|---|
| Barrier Agent | 0.5-2.0% w/w |
| Glycerol (humectant) | 6.0 |
| Pluronic F-108 | 1.0 |
| Sodium saccharin (sweetener) | 0.3 |
| Deionized Water | q.s. |
| Flavors | 1.0 |
| | 100.0 |

EXAMPLE B - Mouthwash Solution

| | |
|---|---|
| Plaque Barrier Agent | 0.5-3.0% w/w |
| Ethanol, USP | 15.0 |
| Pluronic F-108 (foaming agent) | 2.0 |
| Glycerol (humectant) | 10.0 |
| Sorbitol (humectant) | 10.0 |
| Sodium saccharin (sweetener) | 0.2 |
| Deioinzed Water | q.s. |
| Flavors | 0.2 |
| | 100.0 |

EXAMPLE C - Abrasive Dentrifice Gel

| | |
|---|---|
| Plaque Barrier Agent | 2.0-10.0% w/w |
| Fumed Silica (abrasive) | 55.0 |
| Sodium Lauryl Sulfate (detergent) | 1.5 |
| Glycerol (humectant) | 10.0 |
| Carboxymethylcellulose (gelling agent) | 2.0 |
| Sodium saccharin (sweetener) | 0.2 |
| Sorbitol (humectant) | 10.0 |
| Flavors | 1.0 |
| Deionized Water | q.s. |
| Preservative | 0.05 |
| | 100.0 |

EXAMPLE D - Chewing Gum

| | |
|---|---|
| Plaque Barrier Agent | 1.0-11.0% w/w |
| Gum Base | 21.3 |
| Sugar | 48.5-58.5 |
| Corn Syrup (Baume 45) | 18.2 |
| Flavors | 1.0 |
| | 100.0 |

EXAMPLE E - Nonabrasive Gel Dentrifice

| | |
|---|---|
| Plaque Barrier Agent | 0.05-30.0% w/w |
| Sorbistat (preservative) | 0.15 |
| Deionized Water | q.s. |
| Silicon Dioxide (gel stabilizer) | 1.0 |
| Pluronic F-127 (gelling agent) | 20.0 |
| Sodium Saccharin | 0.2 |
| Flavors | 1.5 |
| | 100.0 |

EXAMPLE F

The following formulation illustrates a presently preferred nonabrasive gel composition containing a barrier agent in accordance with the present invention.

| Ingredients | % w/w |
|---|---|
| Distilled Water | q.s. |
| Sodium Saccharin (sweetener) | 0.20 |
| Sodium Benzoate (preservative) | 0.30 |
| FD&C Blue #1 (0.1% aq. soln.) | 0.27 |
| D&C Yellow #10 (0.5% aq. soln.) | 0.50 |
| Gelling agent | 18.00 |
| Glycerol (Humectant) | 20.00 |
| Cab-O-Sil M5 (Silicon Dioxide) | 1.00 |
| Plaque Barrier Agent | 5.00 (dry basis) |
| Flavor | 0.80 |
| | 100.0 |

While the details of preparing all of the above formulations are well within the skill of the art, a suggested procedure for preparing the gel formulation of this example will be described for completeness.

In a first container the water, sodium saccharin, sodium benzoate and dyes are mixed. Then the container is put into an ice bath. When the temperature reaches 6° C., the gelling agent is added and the contents mixed slowly until the gelling agent is dissolved. Then the solution is heated to 70° C.

Into a second container is added the glycerin. Then the Cab-O-Sil M5 is sprinkled in with mixing. Then the plaque barrier agent is added and mixing continued to a smooth paste. The paste is then heated in a water bath with mixing to a temperature of 70° C.

The contents of the first container are added to the second container and blended together until the batch is homogenous while maintaining a 70° C. temperature. Then the flavoring is added, all mixing is stopped, and the formulation allowed to settle for approximately one hour. If necessary to remove air bubbles, overnight refrigeration may be employed.

While any pharmaceutically acceptable gelling agent that is compatible with the plaque barrier agent may be employed, a presently preferred gelling agent is Pluronic F-127.

These compositions are preferably employed from one to three times daily in a routine oral hygiene program to prevent the attachment of plaque to the teeth.

Variations can, of course, be made without departing from the spirit or scope of the invention.

I claim:

1. An oral hygiene composition comprising an effective amount for preventing deposition of dental plaque on teeth of a sulfonated poly(arylene ether sulfone) polymer having a weight average molecular weight of from about 5,000 to about 200,000 and repeating units selected from the group consisting of structure (A),

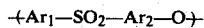 (A)

and structure (B),

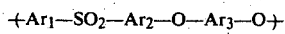 (B)

wherein $Ar_1$ and $Ar_2$ are each selected from

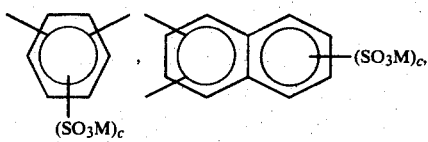

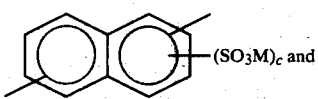

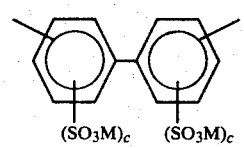

provided further that $Ar_2$ also can comprise one or more spacing units selected from $—Ar_4—SO_2—Ar_4—$ and $Ar_4—SO_2—Ar_4—SO_2—Ar_4—$, each $Ar_4$ in said spacing units being separately selected from

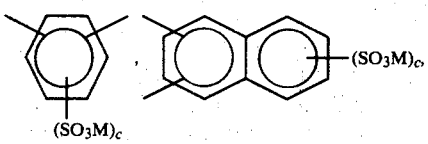

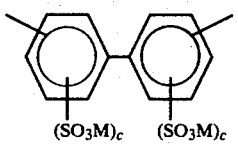

$Ar_3$ is selected from $Ar_4$ and

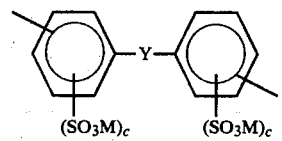

where Y is selected from lower alkylene having 1–5 carbon atoms, lower alkylidine having 2–5 carbon atoms,

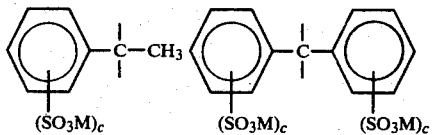

O, S, and $SO_2$; subscript c being an integer selected from 0, 1, and 2, the average quotient obtained by dividing the sum of the c's within each of repeating units (A) and (B) by the number of aromatic groups in said repeating unit being at least about 0.2; and M is selected from the group consisting of lithium, sodium, potassium, calcium, magnesium, zinc, aluminum, hydrogen, ammonium, and substituted ammonium ions derived from pharmaceutically acceptable organic amines, in a pharmaceutically acceptable oral hygiene vehicle compatible with said polymer.

2. The composition of claim 1 wherein M is a metal selected from the group consisting of potassium, lithium, sodium, calcium, magnesium, zinc and aluminum.

3. The composition of claim 1 wherein said quotient is in the range of from about 0.2 to about 0.5.

4. A method of preventing deposition of dental plaque on teeth comprising periodically applying to the teeth a composition of claim 1.

5. The method of claim 4 wherein said composition is applied from about 1 to about 3 times per day.

6. The composition of claim 1 in the form of an oral hygiene formulation selected from the group consisting of mouthwashes, mouthrinses, irrigating solutions, abrasive gel dentifrices, non-abrasive gel dentifrices, denture cleansers, coated dental floss, coated interdental stimulators, chewing gums, lozenges, breath fresheners, foams and sprays.

* * * * *